US012745957B2

(12) United States Patent
Moller et al.

(10) Patent No.: US 12,745,957 B2

(45) Date of Patent: Sep. 29, 2026

(54) SYSTEMS FOR IMPROVING BLOOD CIRCULATION

(71) Applicant: TINKER DESIGN LIMITED, Pinner Middlesex (GB)

(72) Inventors: Christopher Harding Moller, Cottenham (GB); Thushara Sabreen, Pinner Middlesex (GB); Jussi Ville Mikkonen, Vejle (DK)

( * ) Notice: Subject to any disclaimer, the term of this patent is extended or adjusted under 35 U.S.C. 154(b) by 995 days.

(21) Appl. No.: 17/284,514

(22) PCT Filed: Oct. 10, 2019

(86) PCT No.: PCT/GB2019/052887

§ 371 (c)(1),
(2) Date: Apr. 12, 2021

(87) PCT Pub. No.: WO2020/074910

PCT Pub. Date: Apr. 16, 2020

(65) Prior Publication Data

US 2021/0368910 A1 Dec. 2, 2021

(30) Foreign Application Priority Data

Oct. 12, 2018 (GB) .................................... 1816667

(51) Int. Cl.

*A61H 23/02* (2006.01)
*A43B 3/35* (2022.01)

(Continued)

(52) U.S. Cl.

CPC .............. *A61B 5/6807* (2013.01); *A43B 3/35* (2022.01); *A43B 7/146* (2013.01); *A61H 23/02* (2013.01);

(Continued)

(58) Field of Classification Search

CPC .... A61H 23/00; A61H 23/02; A61H 23/0254; A61H 39/02; A61H 39/04;

(Continued)

(56) References Cited

U.S. PATENT DOCUMENTS 5,894,682 A * 4/1999 Broz .................... A43B 13/12 36/31
5,970,630 A * 10/1999 Gallegos ................ A43B 3/24 36/102

(Continued)

FOREIGN PATENT DOCUMENTS

CN 106418872 A 2/2017
CN 108606395 A 10/2018

(Continued)

OTHER PUBLICATIONS

Search Report under Section 17(5) issued in GB Application No. GB1816667.8 on Apr. 12, 2019, 05 pages.

(Continued)

*Primary Examiner* — Bradley H Philips
*Assistant Examiner* — Tyler A Raubenstraw
(74) *Attorney, Agent, or Firm* — RC Trademark Company

(57) ABSTRACT

A system for improving blood circulation, the system comprising a control unit comprising a processor and at least one article of footwear wherein one or more of the at least one articles of footwear together or alone comprise: one or more actuators coupled to and controlled by the control unit; one or more electrically-conductive paths; one or more sensors integrated into the at least one article of footwear and coupled to the processor, for providing measurement signals to the control unit; and the system further comprising an electrical power supply for supplying electrical power to the one or more sensors by means of the one or more electrically-conductive paths.

20 Claims, 16 Drawing Sheets

(51) Int. Cl.

| | |
|---|---|
| ***A43B 7/1455*** | (2022.01) |
| ***A61B 5/00*** | (2006.01) |
| ***A61H 39/00*** | (2006.01) |
| ***A61H 39/04*** | (2006.01) |
| ***B33Y 80/00*** | (2015.01) |

(52) U.S. Cl.
CPC ........... *A61H 39/007* (2013.01); *A61H 39/04* (2013.01); *B33Y 80/00* (2014.12); *A61H 2201/0207* (2013.01); *A61H 2201/164* (2013.01); *A61H 2201/165* (2013.01); *A61H 2201/5007* (2013.01); *A61H 2201/5061* (2013.01); *A61H 2201/5071* (2013.01); *A61H 2201/5082* (2013.01); *A61H 2201/5084* (2013.01); *A61H 2201/5097* (2013.01); *A61H 2205/125* (2013.01); *A61H 2230/08* (2013.01); *A61H 2230/30* (2013.01); *A61H 2230/50* (2013.01)

(58) Field of Classification Search
CPC ...... A61H 2201/0207; A61H 2201/164; A61H 2201/165; A61H 2201/5007; A61H 2201/5061; A61H 2201/5071; A61H 2201/5082; A61H 2201/5084; A61H 1/005; A61H 39/007; A61H 2201/5002; A61H 2201/5058; A61H 2201/5043; A61H 2230/30; A43B 7/146; A43B 3/35; A43B 3/101; A61B 5/6807
See application file for complete search history.

(56) References Cited

U.S. PATENT DOCUMENTS

| | | | | |
|---|---|---|---|---|
| 6,381,482 | B1 * | 4/2002 | Jayaraman | D06M 15/55 600/388 |
| 7,225,565 | B2 * | 6/2007 | DiBenedetto | A43B 3/34 36/29 |
| 7,347,831 | B2 * | 3/2008 | Chiu | A43B 3/35 36/2.6 |
| 8,322,055 | B1 * | 12/2012 | Saint-Cyr | A43B 7/146 36/141 |
| 8,584,382 | B2 * | 11/2013 | Holzer | A43B 3/48 36/137 |
| 2001/0049890 | A1 * | 12/2001 | Hirsch | A43B 13/18 36/25 R |
| 2004/0173220 | A1 * | 9/2004 | Harry | A43B 7/00 128/892 |
| 2008/0161734 | A1 * | 7/2008 | Blockton | A43B 3/35 36/141 |
| 2008/0287832 | A1 * | 11/2008 | Collins | A61B 5/1038 600/587 |
| 2009/0005834 | A1 * | 1/2009 | Weintraub | A61H 23/0263 601/48 |
| 2010/0186255 | A1 * | 7/2010 | Avar | A43B 17/16 36/25 R |
| 2011/0009713 | A1 * | 1/2011 | Feinberg | A63B 21/065 482/8 |
| 2011/0232134 | A1 * | 9/2011 | Radl | A61F 5/14 36/141 |
| 2012/0291563 | A1 * | 11/2012 | Schrock | A43B 3/00 73/862.041 |
| 2014/0070957 | A1 | 3/2014 | Longinotti-Buitoni et al. | |
| 2015/0088057 | A1 * | 3/2015 | Su | A61B 5/746 604/66 |
| 2015/0100105 | A1 * | 4/2015 | Kiani | A61N 1/36003 607/49 |
| 2015/0330855 | A1 * | 11/2015 | Daniecki | A61B 5/6807 73/725 |
| 2016/0067584 | A1 * | 3/2016 | Giedwoyn | G16H 40/67 700/91 |
| 2016/0206500 | A1 * | 7/2016 | Steinlauf | A61H 9/0078 |
| 2016/0263375 | A1 | 9/2016 | Wu | |
| 2016/0317370 | A1 * | 11/2016 | Evans | G05B 15/02 |
| 2017/0017264 | A1 | 1/2017 | Vacas Jacques | |
| 2017/0105476 | A1 * | 4/2017 | Morrison | A61B 5/6807 |
| 2017/0112200 | A1 * | 4/2017 | Mason | H01R 13/052 |
| 2017/0127999 | A1 * | 5/2017 | Linders | G16H 50/20 |
| 2017/0156655 | A1 * | 6/2017 | Austin | A61B 5/18 |
| 2017/0188841 | A1 * | 7/2017 | Ma | A61B 5/01 |
| 2017/0265560 | A1 | 9/2017 | Beers et al. | |
| 2018/0206586 | A1 * | 7/2018 | Akay | A43B 3/34 |
| 2018/0213879 | A1 * | 8/2018 | Campbell | A43B 3/36 |
| 2018/0271209 | A1 * | 9/2018 | Zahrieh | A61H 39/007 |
| 2019/0000329 | A1 * | 1/2019 | Denson | A61H 9/0092 |
| 2019/0099312 | A1 * | 4/2019 | Laasanen | A61G 10/02 |
| 2020/0359735 | A1 * | 11/2020 | Cho | B06B 1/045 |

FOREIGN PATENT DOCUMENTS

| | | | |
|---|---|---|---|
| DE | 102009033510 | A1 | 5/2010 |
| WO | 2006113918 | A2 | 10/2006 |
| WO | 2008061023 | A2 | 5/2008 |
| WO | 2008061023 | A3 | 7/2008 |
| WO | 2009152456 | A2 | 12/2009 |
| WO | 2010091258 | A1 | 8/2010 |
| WO | 2012109244 | A1 | 8/2012 |
| WO | 2014100045 | A1 | 6/2014 |
| WO | 2014138204 | A1 | 9/2014 |
| WO | 2016130888 | A1 | 8/2016 |
| WO | 2016198969 | A1 | 12/2016 |
| WO | 2017095026 | A1 | 6/2017 |
| WO | 2017190049 | A1 | 11/2017 |
| WO | 2018200798 | A1 | 11/2018 |

OTHER PUBLICATIONS

International Search Report and Written Opinion of the International Searching Authority mailed in PCT Application No. PCT/GB2019/052887 on Mar. 31, 2020, 18 pages.
Search Report under Section 17(5) issued in GB Application No. GB1914681.0 on Apr. 20, 2020, 06 pages.
Communication pursuant to Article 94(3) EPC issued for European Patent Application EP21156319.2, on Dec. 21, 2023, 09 Pages.

* cited by examiner

SYSTEMS FOR IMPROVING BLOOD CIRCULATION

FIELD OF THE INVENTION

The present invention relates to systems for improving blood circulation, comprising at least one article of footwear having electronic functionality.

BACKGROUND TO THE INVENTION

Articles of footwear having electronic functionality are being developed. There is a desire to improve these to achieve enhanced functionality and to realise new applications.

SUMMARY OF THE INVENTION

According to a first aspect of the invention there is provided a system for improving blood circulation, the system comprising a control unit comprising a processor and at least one article of footwear, wherein one or more of the at least one articles of footwear together or alone comprise: one or more actuators coupled to and controlled by the control unit; and a flexible wearable material comprising: one or more electrically-conductive paths; and one or more sensors integrated into the wearable material and coupled to the processor, for providing measurement signals to the control unit; the system further comprising an electrical power supply for supplying electrical power to the one or more sensors by means of the one or more electrically-conductive paths.

Optionally, the article of footwear further comprises a rigid base.

Optionally, the rigid base comprises one or more recesses for receiving one or more of said actuators and/or one or more base sensors.

Optionally, the flexible wearable material comprises at least one elastic fibre for providing pressure around the circumference of the foot.

Optionally, the one or more sensors integrated into the wearable material comprise a pressure sensor for measuring blood pressure.

Optionally, the control unit is configured to activate the one or more actuators in response to a measurement signal received from the one or more sensors satisfying a predetermined condition.

Optionally, the flexible wearable material comprises a knitted or woven fabric.

Optionally, the one or more electrically-conductive paths are formed of electrically-conductive yarn within the fabric.

Optionally, the one or more sensors are attached to the electrically-conductive yarn.

Optionally, the article of footwear comprises a 3D-printed material.

Optionally, the electrical power supply comprises a battery.

Optionally, the electrical power supply comprises an input via which electrical power may be received from elsewhere.

Optionally, the one or more sensors are selected from a group comprising: pressure sensors, temperature sensors, biosensors, moisture sensors, accelerometers and inclinometers.

Optionally, the one or more actuators comprise one or more motors (e.g. eccentric motors).

Optionally, the one or more motors are configured to provide a vibration/massage function.

Optionally, the one or more actuators comprise one or more heating elements.

Optionally, said at least one article of footwear is a massage shoe.

Optionally, said at least one article of footwear is a slipper.

Optionally, said at least one article of footwear is a sock, or a tubular article open at both ends for sheathing a limb, or a tubular article open at one end for sheathing a limb.

Optionally, said at least one article of footwear is a boot, sock or pad for an animal's foot/hoof/paw.

Optionally, said at least one article of footwear comprises a first article of footwear and a second article of footwear, wherein the first article of footwear is a shoe and the second article of footwear is a sock.

Optionally, the said sock comprises the said flexible wearable material comprising the one or more sensors and the said shoe comprises the said one or more actuators.

Optionally, at least one of the at least one article of footwear comprises an insole.

Optionally, the insole comprises at least one electrically conductive foil to provide a said electrically-conductive path.

Optionally, the at least one electrically conductive foil is arranged to receive and/or distribute electrical power multiplexed with at least one data signal.

Optionally, the insole comprises at least one recess for receiving at least one button.

Optionally, the insole further comprises at least one sensor button and/or at least one actuator button.

Optionally, the at least one recess is circular.

Optionally, at least one of the at least one article of footwear comprises a cushioning layer located between the insole and the flexible wearable material.

Optionally, the vibration/massage function comprises a tailored massage.

Optionally, the tailored massage comprises a vibration/massage localised to an area of the sole of a user.

Optionally, the control unit is configured to identify high stress points from the measurement signals received from the one or more sensors.

Optionally, the area of the sole of a user comprises high stress points.

Optionally, the system further comprises a mobile application configured to display the high stress points.

Optionally, the mobile application is further configured to receive instructions from a user to massage specific points of the sole of the said user's foot.

Optionally, the system is configured to improve mobility, to aid in muscle recovery, to reduce knee, foot or lower back pain and/or to enhance the comfort of a user.

Optionally, the system for use in the treatment of at least one of the following: knee pain; foot pain; and/or lower back pain.

Optionally, the system is configured to predetermine a treatment for preventative care.

Optionally, at least one of the conductive-paths, conductive yarn or conductive foil comprise graphene.

According to a second aspect of the invention there is provided a system for improving blood circulation, the system comprising a control unit comprising a processor and at least one article of footwear wherein one or more of the at least one articles of footwear together or alone comprise: one or more actuators coupled to and controlled by the control unit; one or more electrically-conductive paths; one or more sensors integrated into the at least one article of footwear and coupled to the processor, for providing measurement signals to the control unit; and the system further comprising an electrical power supply for supplying electrical power to the one or more sensors by means of the one or more electrically-conductive paths.

The term "processor" as used herein should be interpreted broadly, to encompass a general purpose processor, the processor of an application specific integrated circuit, a microprocessor, a digital signal processor, a controller, a microcontroller, a state machine, and so on. The term "processor" may also refer to a plurality of such processing devices in combination.

More generally, in some embodiments the electrical power supply may comprise a battery. Alternatively, or in addition, the electrical power supply may comprise an input via which electrical power may be received from elsewhere (e.g. by means of an electrical power supply cable).

The one or more sensors may be selected from a group comprising: pressure sensors, temperature sensors, biosensors, moisture sensors, accelerometers and inclinometers. Other types of sensors may also be used, as those skilled in the art will appreciate.

The one or more actuators may comprise one or more motors and/or one or more heating elements. Advantageously, the one or more motors may be configured to provide a vibration/massage function. Other types of actuators may also be provided, as those skilled in the art will appreciate.

Other embodiments and applications are also possible, as described herein, and as those skilled in the art will appreciate.

BRIEF DESCRIPTION OF THE DRAWINGS

Embodiments of the invention will now be described, by way of example only, and with reference to the drawings in which.

In the figures, like elements are indicated by like reference numerals throughout.

DETAILED DESCRIPTION OF PREFERRED EMBODIMENTS

Overview

Figure 1:
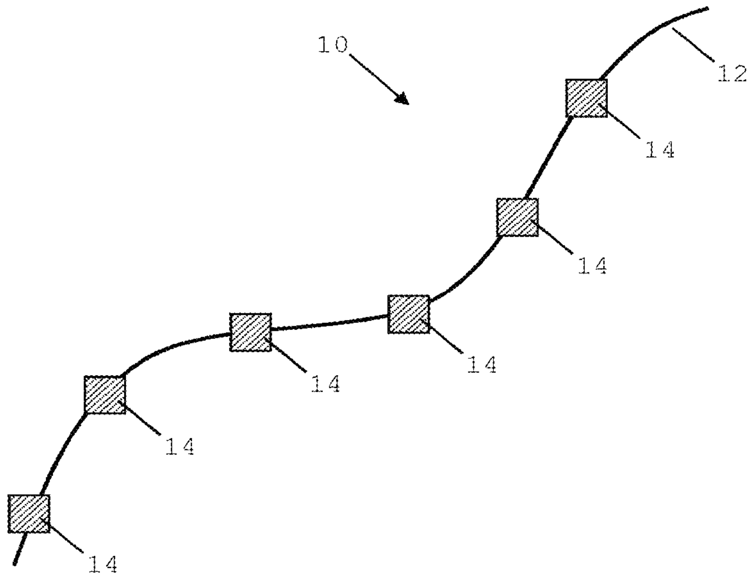
FIG. 1 illustrates an electrically-conductive yarn with a plurality of sensors attached.

The present work provides a system for improving blood circulation including a control unit comprising a processor and at least one article of footwear. The at least one articles of footwear, together or alone, comprise one or more actuators coupled to and controlled by the control unit and a flexible wearable material. The flexible wearable material comprises one or more electrically-conductive paths and one or more sensors integrated into the wearable material and coupled to the processor for providing measurement signals to the control unit. The system further comprises an electrical power supply for supplying electrical power to the one or more sensors by means of the one or more electrically-conductive paths.

The present work also provide for a system for improving blood circulation, the system comprising a control unit comprising a processor and at least one article of footwear wherein one or more of the at least one articles of footwear together or alone comprise: one or more actuators coupled to and controlled by the control unit; one or more electrically-conductive paths; one or more sensors integrated into the at least one article of footwear and coupled to the processor, for providing measurement signals to the control unit; and the system further comprising an electrical power supply for supplying electrical power to the one or more sensors by means of the one or more electrically-conductive paths.

A system of the present work may include a single article of footwear or several articles working together and should therefore the term "system" should be interpreted broadly to mean one or more apparatus working together.

The components of the one or more articles of footwear of the system may be components of a single article of footwear, components of each of several articles of footwear or may be components shared between several articles of footwear.

The present work also provides flexible wearable material (preferably comprising knitted or woven fabric, or alternatively flexible 3D-printed material) which includes electrically conductive parts or paths (e.g. conductive yarns) and non-conductive parts or paths (e.g. non-conductive yarns), a processor, an electrical power supply (e.g. a battery, or an input via which electrical power may be received from elsewhere), one or more sensors (integrated into the fabric), and one or more actuators (e.g. to provide massage functionality or for haptic purposes). The fabric may be knitted or woven in, for example, (a) an open form, intended for wrapping around a limb; (b) a tubular form open at both ends, intended for sheathing a limb; or (c) a tubular form open at one end only, intended for sheathing a limb.

The fabric may have one or more conductive and non-conductive areas or paths made from different types of yarns, filaments or other suitable textile materials. The fabric may also comprise other electro-active materials and/or other electrical or electronic components.

The wearable material has a range of application areas, including for use in healthcare. For example, a woven or knitted structure according to an embodiment of the invention may be used for real-time analysis, and may provide connectivity to smart phones or other systems, e.g. through wireless data transfer. Artificial Intelligence may be used to interpret the readings from the sensors and to control the operation of the actuators. Embodiments may be provided for independent as well as connected behaviour.

Advantageously, the wearable material can be attached to a limb (in the form of a shoe, for example, or some other structure to be worn for ambulatory movement) in such a way that it does not inhibit the movement of the wearer, whilst providing electronic functionality (including sensing functionality and, preferably, actuation functionality).

Electrically-Conductive Yarn with Sensors Attached

FIG. 1 illustrates, as identified by numeral 10, an electrically-conductive yarn 12 with a plurality of sensors 14 attached, that may be used to produce “smart material” fabric. Although, in the illustrated example, a plurality of sensors 14 are attached to the electrically-conductive yarn 12, in an alternative example a single sensor 14 may be attached to the yarn 12. Suitable electrically-conductive yarns include the so-called “Volt Smart Yarns” supplied by Supreme Corporation, 325 Spencer Road, Conover, N.C. 28613, USA.

The electrically-conductive yarn 12 is preferably copper-based, and is stretchable and flexible. The or each sensor 14 may be attached to the electrically-conductive yarn 12 using a placement machine. It is then encapsulated to seal the sensor 14 onto the yarn. The electrically-conductive yarn 12 may be provided with a non-conductive coating (e.g. a plastic coating).

The or each sensor 14 may be, for example, a pressure sensor, a temperature sensor or a moisture sensor, although other types of sensors are also possible, such as biosensors (e.g. to measure heart rate), accelerometers and inclinometers. The functionality and exemplary applications of different types of possible sensors are described in greater detail below.

As also discussed in greater detail below, the or each sensor 14 receives electrical power via the electrically-conductive yarn 12. As illustrated in FIG. 1, a plurality of sensors 14 may be wired in series along the electrically-conductive yarn 12, so that they are all powered by the same length of yarn. The or each sensor 14 may also send its measurement readings (e.g. pressure measurements, temperature measurements, moisture measurements) via electrically-conductive yarn. A plurality of different types of sensors may be provided along a given length of electrically-conductive yarn.

“Smart Material” Fabric

Figure 2:
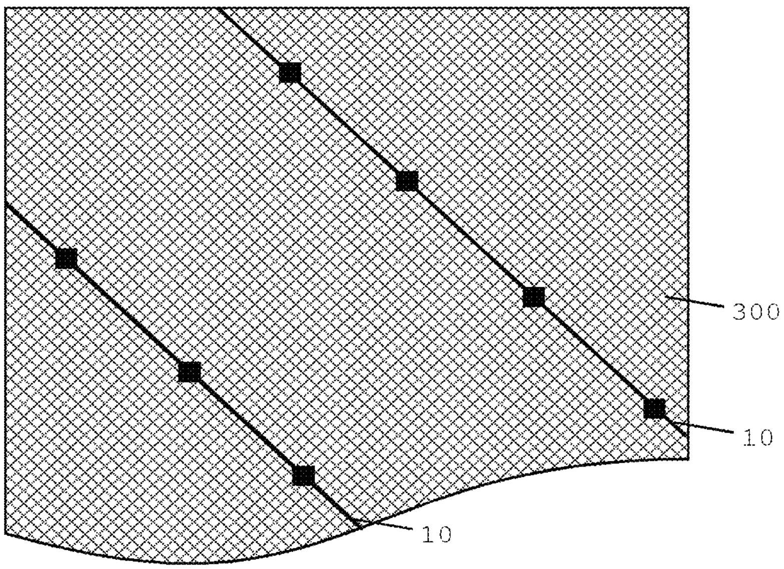
FIG. 2 illustrates a piece of fabric (so-called "smart material", which may be knitted or woven, for example) incorporating a plurality of lengths of yarn as depicted in FIG. 1 with sensors attached.

FIG. 2 illustrates a piece of flexible knitted or woven fabric 300 (so-called “smart material” fabric) incorporating a plurality of lengths of yarn 10, each length of yarn 10 being electrically-conductive and having one or more sensors 14 attached—for example as described above with reference to FIG. 1. Although, in the illustrated example, a plurality of lengths of such yarn 10 are shown, in an alternative example a single length of yarn 10 may be incorporated in the fabric 300. Preferably, though, a plurality of lengths of such yarn 10 may be used, e.g. to produce a two-dimensional array of sensors across the fabric.

The length(s) of yarn 10 that are electrically-conductive and have one or more sensors 14 attached are knitted or woven into the fabric 300 among other non-conductive lengths of yarn. The non-conductive lengths of yarn may be, for example, wool, cotton, or a synthetic fibre.

Example Implementations

Figure 3:
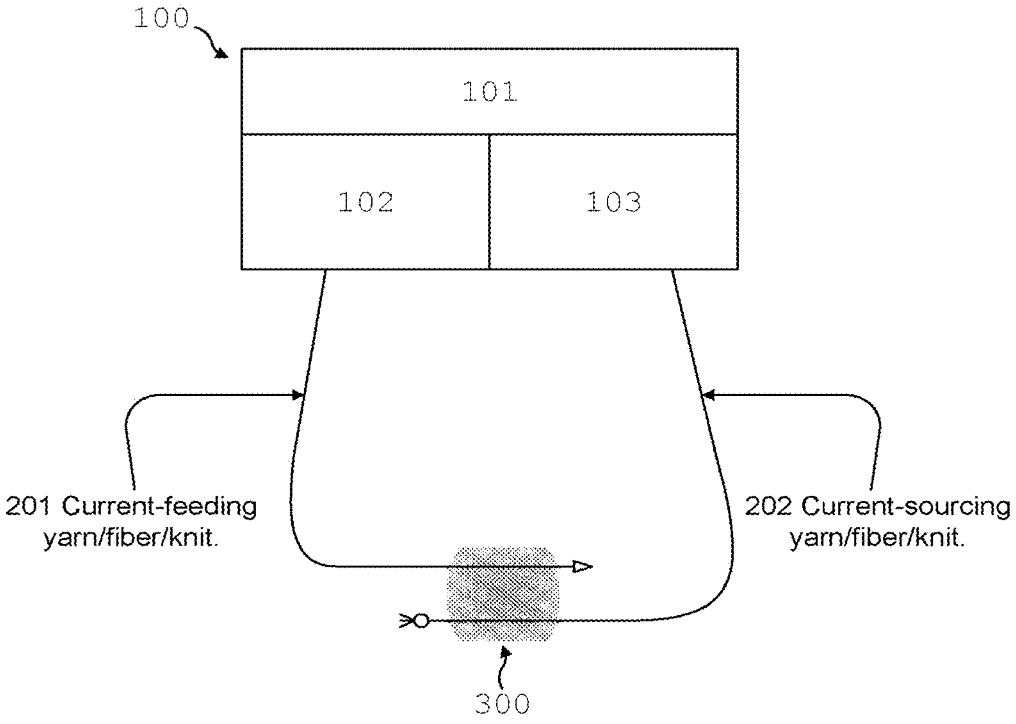
FIG. 3 schematically illustrates apparatus comprising a piece of smart material as depicted in FIG. 2, to which a control module, a power supply module and an analysis module are coupled by means of appropriate circuitry.

FIG. 3 schematically illustrates apparatus comprising a piece of smart material 300 (for example as described above with reference to FIG. 2), to which a control module 101, a power supply module 102 and an analysis module 103 are coupled by means of appropriate circuitry. Together, the control module 101, power supply module 102 and analysis module 103 form a control unit 100.

The control module 101 includes a processor and is configured to control the power supply module 102 and the analysis module 103. It may also be configured to make operational decisions and to perform top-level analysis.

The power supply module 102 (which may also comprise a processor) is configured to supply electrical power to the smart material 300 (specifically, to the sensors thereof) by means of a conductive yarn/fibre/knit 201. The power supply module 102 may receive electrical power from a battery or from elsewhere, e.g. by means of an electrical power supply cable. It is expressly contemplated, for instance, that certain embodiments may draw current via a plugged-in USB cable or the like, e.g. of the order of 500 mA to 5 A.

The analysis module 103 (which may also comprise a processor) is configured to receive measurement signals from the sensor(s) of the smart material 300 by means of a conductive yarn/fibre/knit 202 and to analyse them, for example to determine quantitative measurements of e.g. pressure or temperature. However, depending on the sensor type and the intended application, the output from a particular sensor may alternatively be qualitative or binary (e.g. in the case of a moisture sensor, is moisture present or not?). If the smart material 300 comprises a plurality of sensors, then preferably the positions of the individual sensors are known to the analysis module, so that it can determine location-specific measurements. For instance, the sensors may be addressable.

The smart material 300 may for example be an insole of a shoe, although many other applications are also possible. Advantageously, the smart material 300 may be exchangeable, and the measurement system may user-adjustable, to cater for users of different weights, different pressure configurations, different moisture levels, etc.).

Implementations based on FIG. 3 may comprise any number of control units 100 and sensors, with a minimal implementation having one of each. Control unit 100 may comprise modules 101, 102 and 103, but it is not necessary for these to be separate modules. Any part of the overall apparatus may include a power supply (e.g. a battery or other electronic component, or an input to receive power from elsewhere).

Figure 4:
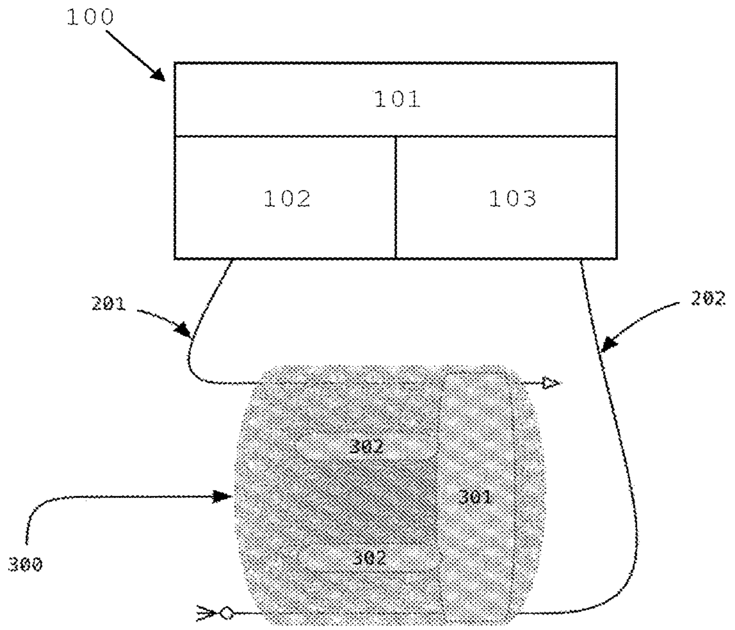
FIG. 4 schematically illustrates apparatus comprising a piece of smart material as depicted in FIG. 2, to which a control module, a power supply module, an analysis module and a plurality of actuators are coupled by means of appropriate circuitry.

As another implementation, FIG. 4 schematically illustrates apparatus comprising a piece of smart material 300 (for example as described above with reference to FIG. 2), to which a control module 101, a power supply module 102, an analysis module 103 and a plurality of actuators 302 are coupled by means of appropriate circuitry. The smart material 300 may for example be an insole of a shoe, although many other applications are also possible. Although, in the illustrated implementation, a plurality of actuators 302 are provided, in an alternative implementation a single actuator 302 may be provided. Together, the control module 101, power supply module 102 and analysis module 103 form a control unit 100. As illustrated, the smart material 300 also includes an optional module 301 for identifying the overall component (e.g. a specific insole of a shoe) that includes the smart material. The module 301 may (but not necessarily) include a memory and/or a processor for controlling the properties of the component (e.g. insole).

The control module 101 includes a processor and is configured to control the power supply module 102 and the analysis module 103. In the case of the overall component which includes the smart material being an insole, the control module 101 may analyse what the insole is built into, and may analyse wear and tear of the insole.

As described above, the power supply module 102 is configured to supply electrical power to the smart material 300 (specifically, to the sensors thereof) by means of a conductive yarn/fibre/knit 201. The power supply module 102 may receive electrical power from a battery or from elsewhere, e.g. by means of an electrical power supply cable.

Also as described above, the analysis module 103 (which may also comprise a processor) is configured to receive measurement signals from the sensor(s) of the smart material 300 by means of a conductive yarn/fibre/knit 202 and to analyse them, for example to determine quantitative measurements of e.g. pressure or temperature. However, depending on the sensor type and the intended application, the output from a particular sensor may alternatively be qualitative or binary (e.g. in the case of a moisture sensor, is moisture present or not?). If the smart material 300 comprises a plurality of sensors, then preferably the positions of the individual sensors are known to the analysis module, so that it can determine location-specific measurements. For instance, the sensors may be addressable.

The actuators 302 are electrically-controlled devices, such as motors (e.g. for vibration/massage purposes) or heating elements, which may be activated, under the control of the control unit 100, via the module 301. When used in an article of footwear, such motors may be positioned to coincide with key pressure points (reflexology points) on the foot, to apply vibration/massage to those specific points. The functionality and exemplary applications of different types of possible actuators are described in greater detail below.

The control unit 100 may be configured to activate the actuators 302 (e.g. motors) in response to a measurement signal received from the sensors in the smart material 300 satisfying a predetermined condition—such as, for example, a measured pressure exceeding a predetermined threshold (e.g. indicating a relatively high level of pressure on the foot), or a measured pressure differential across the foot exceeding a predetermined threshold (e.g. indicating a relative imbalance of the foot).

The actuators 302 may be encased in material (e.g. including, but not necessarily, polymers, conductive materials, alloys or combinations of such), active components, or any other devices.

Figure 5:
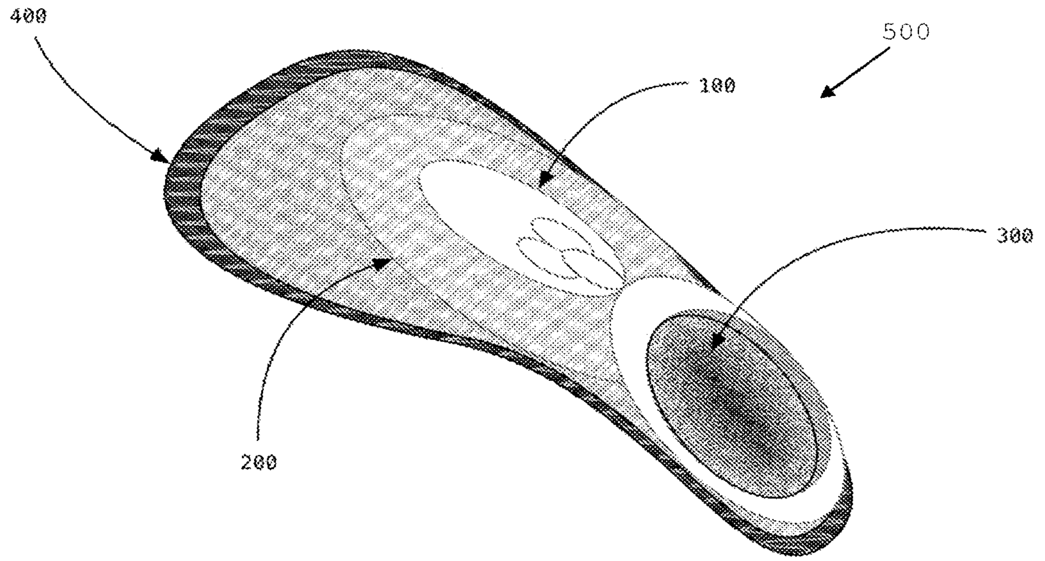
FIG. 5 illustrates a shoe incorporating apparatus as depicted in FIG. 4.
Figure 6:
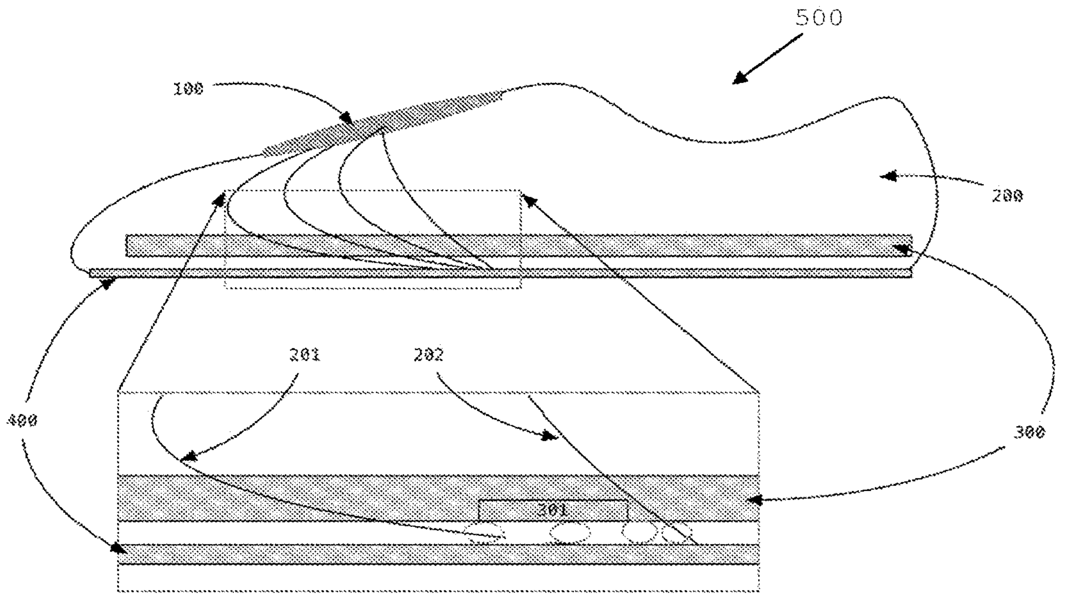
FIG. 6 illustrates a shoe layer and connection diagram in respect of the shoe as depicted in FIG. 5.

FIGS. 5 and 6 illustrate a shoe 500 incorporating apparatus as depicted in FIG. 4.

More particularly, the shoe 500 includes a smart material insole 300 (e.g. as described above) and an outsole 400, which may comprise any suitable material(s). The outsole 400 may also have similar "smart" characteristics and constituent features (e.g. sensors and actuators) to those of the insole 300. Numeral 200 refers to knitted or woven fabric making the shoe, which may consist of any number of conductive yarns/fibres/knits 201 and 202. The shoe 500 also includes a control unit 100 as described above, and, as illustrated, may also include an optional module 301 as described above.

Figure 7:
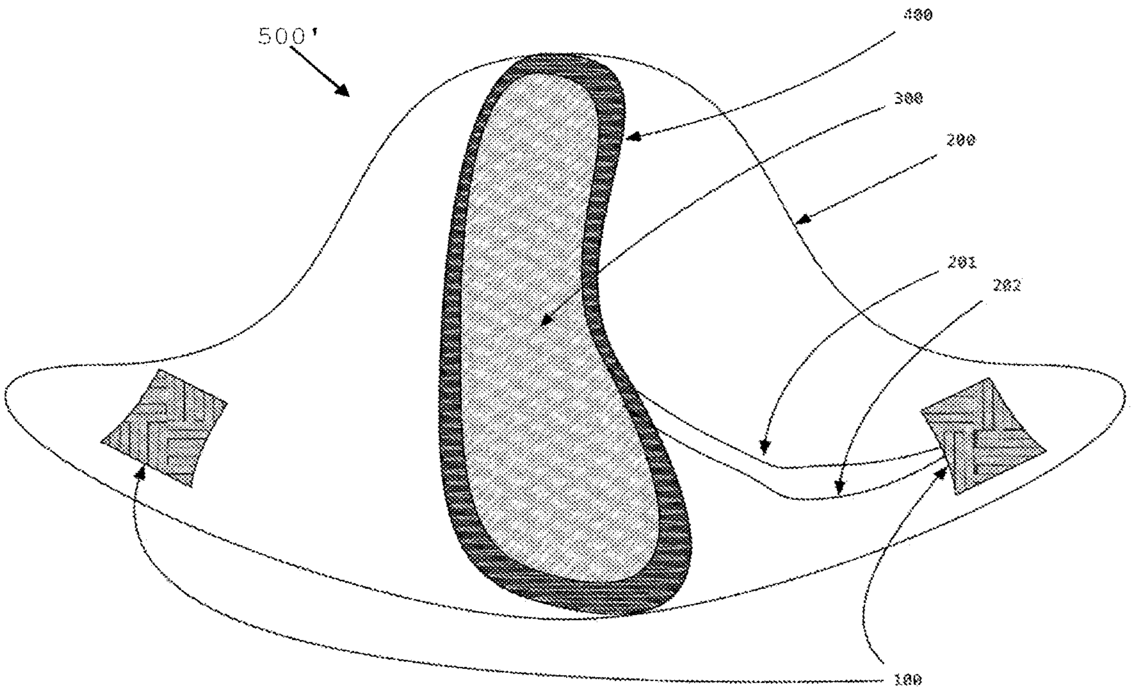
FIG. 7 illustrates another shoe structure incorporating smart material.

FIG. 7 illustrates another embodiment of a shoe 500' incorporating a smart material insole 300 (e.g. as described above) and an outsole 400. Numeral 200 refers to knitted or woven wrap-around fabric making the shoe, which may consist of any number of conductive yarns/fibres/knits 201 and 202. The shoe 500 also includes a control unit 100 which may contain elements 101-103 as described above. These can be split into multiple parts—in this case, provided as two separate units that come together as the wrap-around fabric 200 is folded.

Figure 8:
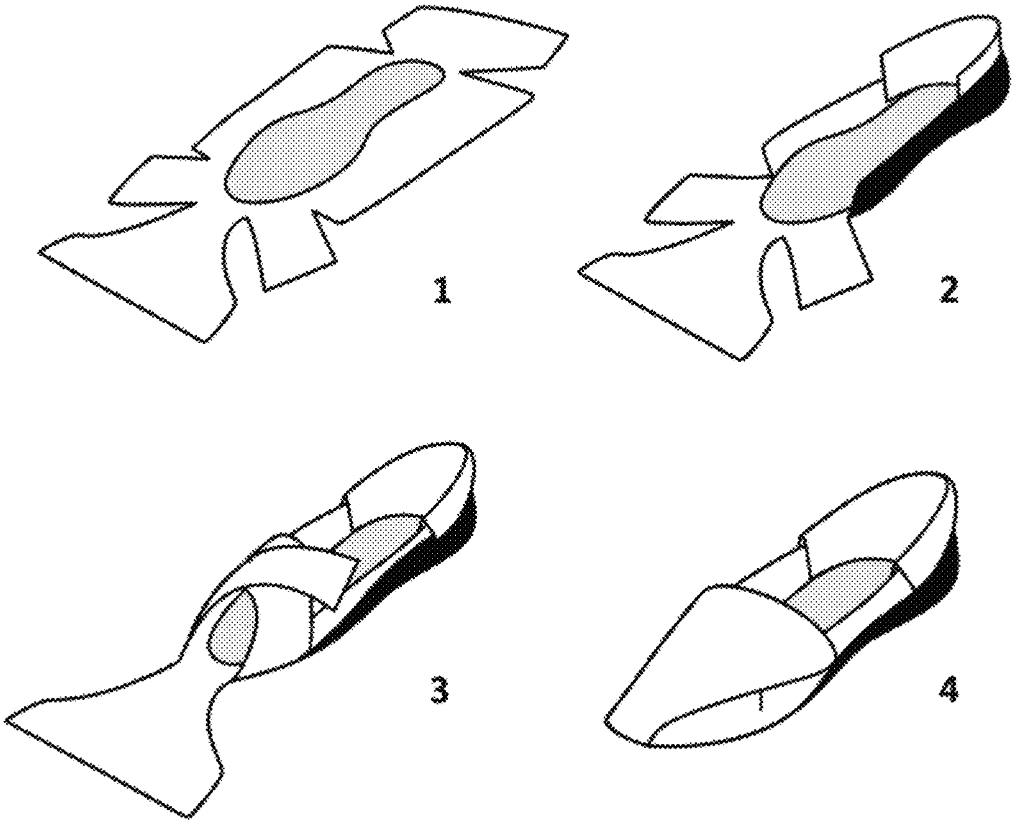
FIG. 8 illustrates another possible shoe structure which may embody the invention, along with the manner of manufacture (folding sequence) of the shoe.

The shoe 500' of FIG. 7 can alternatively be formed as shown in FIG. 8. This shows, as stages 1-4, the sequence by which the wrap-around fabric is folded to make the shoe. The above-described smart material, with sensors and optional actuators, may form any part of the illustrated material (e.g. the insole and/or the outsole).

In alternative implementations the shoe (including the sensors and conductive tracks) can be made using additive manufacturing (3D printing).

Figure 9:
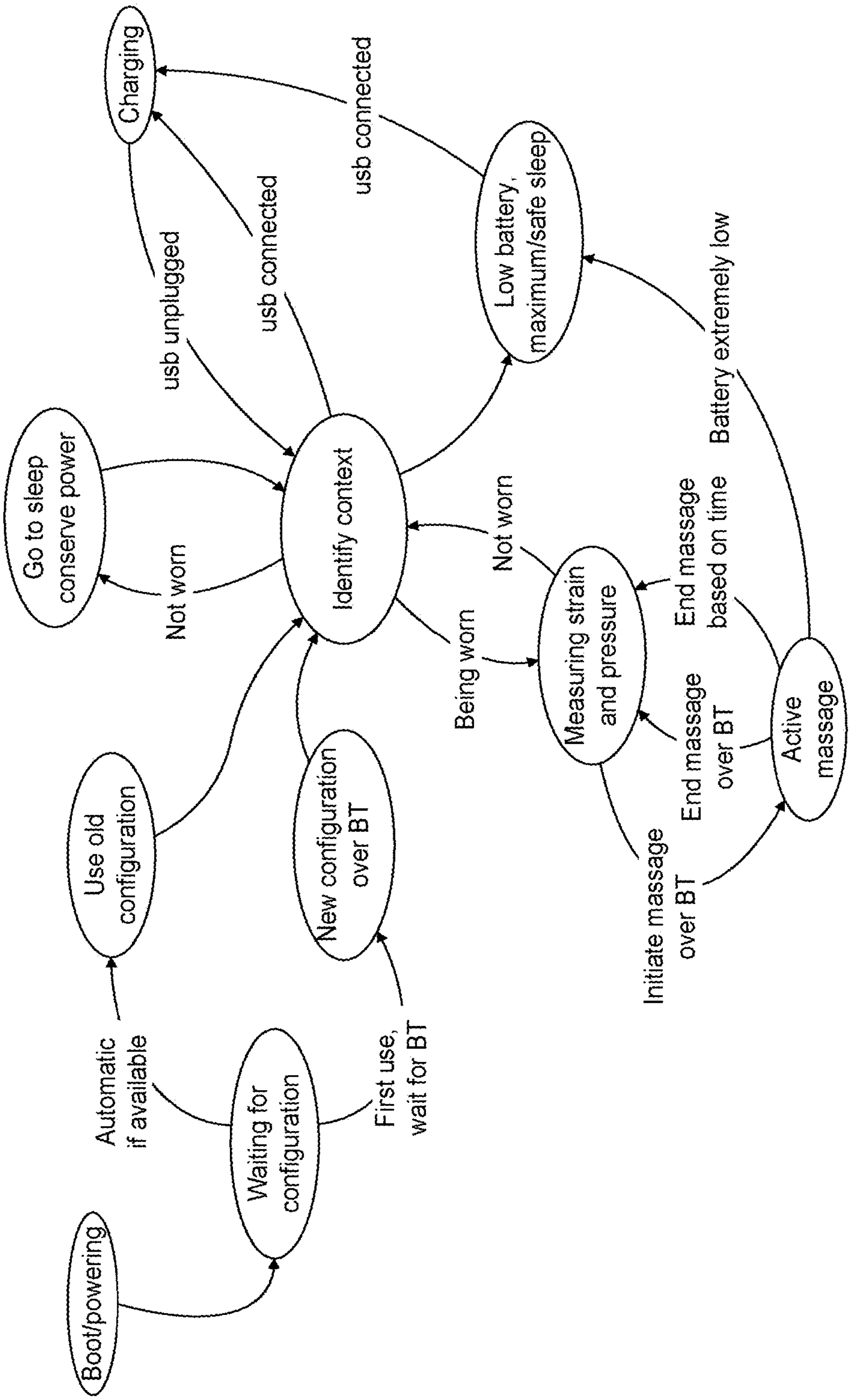
FIG. 9 illustrates an operational flow diagram relating to the use of a wearable device (e.g. a shoe) incorporating smart material with sensors, and having one or more massage-giving actuators.

FIG. 9 is an operational flow diagram relating to the use of a wearable device (e.g. a shoe) incorporating smart material with sensors, and having one or more massage-giving actuators.

Sensor Types and Exemplary Applications

By way of example, the following types of sensors may be used in embodiments of the invention (for example, but not limited to, shoes):

- Pressure sensors (e.g. to measure pressure at different points across the underside of the wearer's foot, and/or to measure the wearer's weight).
- Temperature sensors (e.g. to measure the temperature of the underside of the wearer's foot).
- Biosensors (e.g. to measure the wearer's heart rate).
- Moisture sensors (e.g. to detect the presence of sweat, for example as a result of exercise).
- Accelerometers and inclinometers (e.g. to detect the wearer's posture, gait or speed of movement).

Actuator Types and Exemplary Applications

By way of example, the following types of actuators may be used in embodiments of the invention (for example, but not limited to, shoes):

- Motors (e.g. to provide vibration or massage to the wearer's body (e.g. foot), or haptic feedback to the wearer).

- Heating elements (e.g. to provide heating to the wearer's body (e.g. foot)).

Shoe/Sock Implementation

One implementation of a knitted or woven shoe provides a textile bio-engineering computing platform (textile bioinformatics) incorporating a dynamic adaptive knit structure having anti-microbial and sweat wicking properties. The circuit within the knit structure may be provided with any or all of the following sensors and actuators:

- Knitted temperature sensors.
- Heating elements (e.g. so that the shoe heats up when it senses the wearer's feet are cold).
- Pressure sensors (e.g. to understand daily pressures on the wearer's feet with real-time information).
- Actuators (embedded in the insole) for vibration/massage therapy.
- Biometric sensing—Hydration/Biometric Impedance Analysis (e.g. to monitor the body's water intake levels and how sweat affects hydration to determine the body's water content. This information provides useful insights into the body's hydration levels (total body water) and fat percentage.)

The knitted or woven shoe is developed for healthy and quality lifestyles with functions of protection, prevention, diagnosis and treatment of disease, and for improving health.

The structure of the shoe can be customised via 3D scanning of the person's foot, for extra support and cushioning to achieve an increase in comfort of the individual foot bed.

The shoe preferably houses a rechargeable battery which can be wirelessly charged (e.g. using nano-generation/flexible super capacitors).

A Bluetooth (BT) or other short-range low-power wireless transmitter (e.g. radio frequency identification, RFID) may be incorporated in the shoe, to directly communicate/exchange information with another device (e.g. a smart phone running an app). This may use Augmented Intelligence to nudge the user's behaviour, e.g. with respect to improving their posture.

Alerts may also help to identify when to massage the wearer's feet to ease pressure on the feet (e.g. to treat peripheral neuropathy).

Massage/vibration therapy may be used as an aid to improve circulation and balance (as cold feet, typically caused by poor blood flow, can cause a loss of senses). The shoe can create better awareness of foot health (as poor blood circulation has been linked to chronic health conditions such as high blood pressure, obesity, and diabetes).

Understanding daily pressure on the wearer's feet is important to avoiding irreversible damage. The shoe may provide real-time information which allows the management of this.

By supplying biometric data from the shoe to a doctor (e.g. via a wireless cloud-based platform), the doctor can have the wearer's biometric data to hand before they visit, and can use this data to predict future illness and better treat current illness. For instance, this may potentially prevent wounds and amputations caused by diabetes.

The shoe incorporating a textile computing platform could connect the user to the Internet of Things ("IoT"). This may be used to connecting the wearer to a medical practitioner/health service. An Artificial Intelligence algorithm may be used for the advancement of holistic wellbeing and management of rehabilitation, therapy and preventative care.

Insole Implementation

Figure 10:
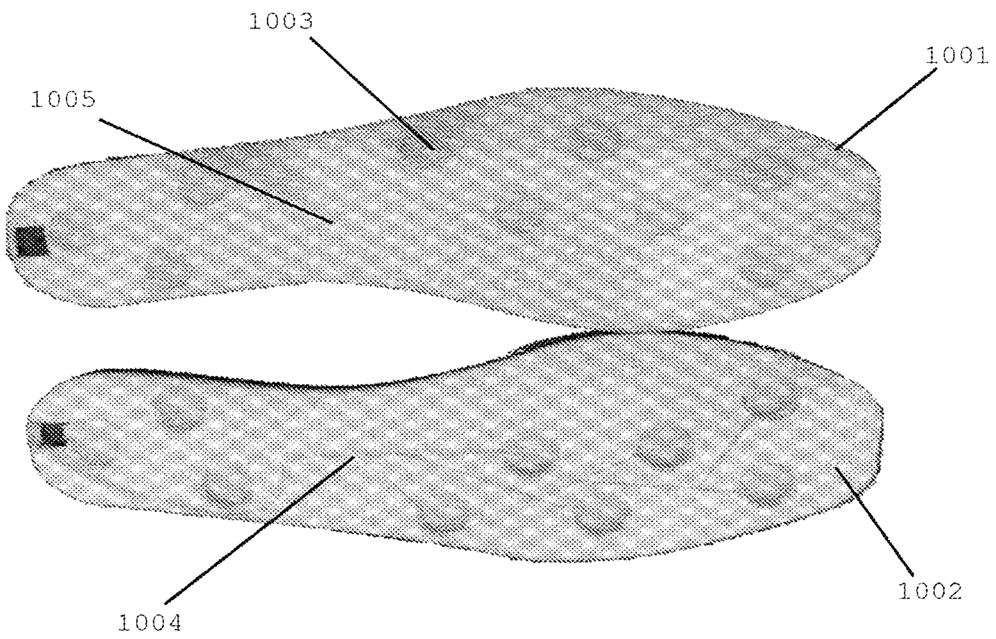
FIG. 10 illustrates two insoles either of which when inserted into a shoe may embody the invention.

As shown in FIG. 10, the invention may be embodied in an insole suitable for placement or incorporation into a shoe, slipper or some other article of footwear. FIG. 10 shows two examples of insoles, a first insole 1001 and a second insole 1002. Both insoles 1001, 1002 include a number of button recesses 1003 which are suitable, and may be shaped, for receiving sensor buttons 1101 (as shown in FIGS. 11 and 12) or actuator buttons 1202 (as shown in FIGS. 12, 13*a* and 13*b*).

In the present embodiment, the sensor buttons may also be known as base sensors by virtue of their location relative to the user's foot (in use). Namely, in use they would be located on the base of the user's foot.

Figure 11:
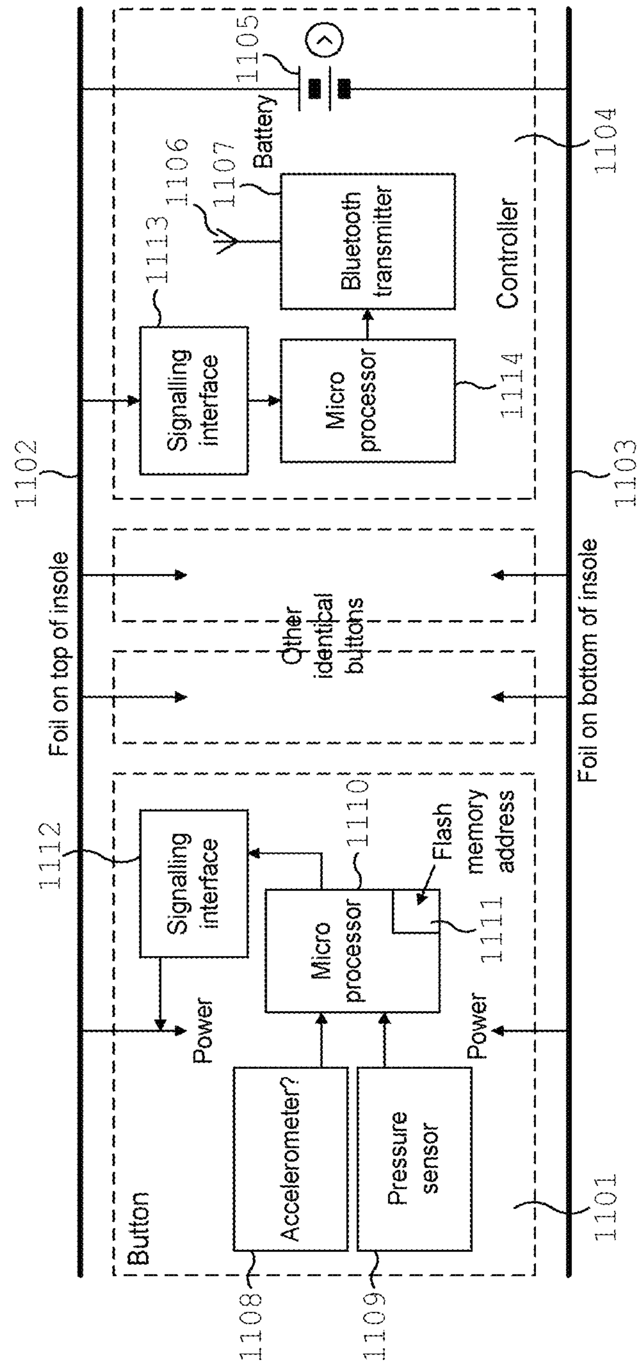
FIG. 11 schematically illustrates a first example of the electrical circuitry of an insole such as the insoles of FIG. 10.
Figure 12:
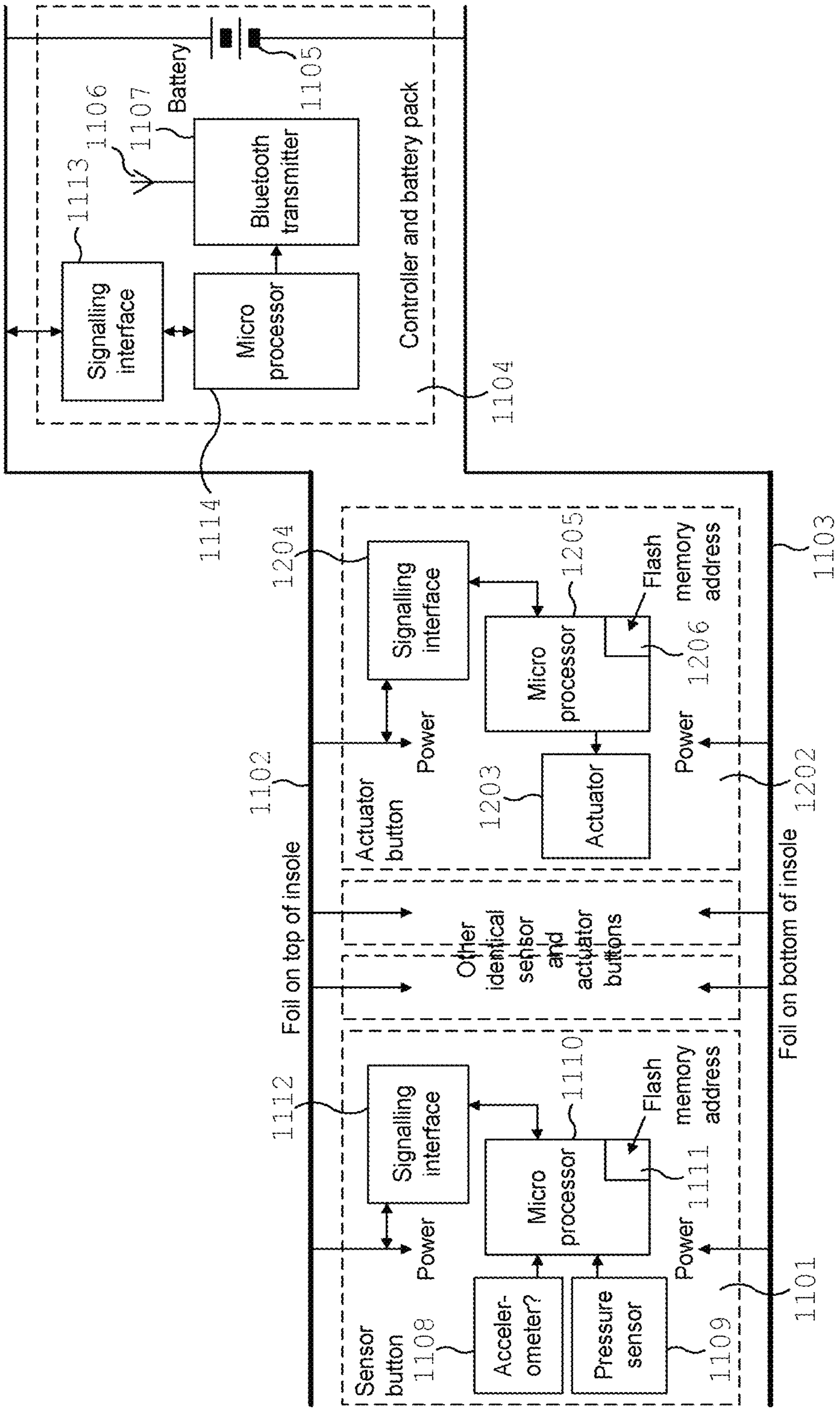
FIG. 12 schematically illustrates a second example of the electrical circuitry of an insole such as the insoles of FIG. 10.
Figure 13B:
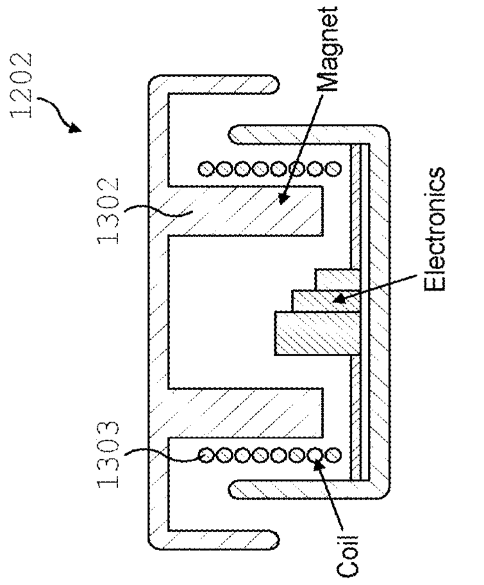
FIG. 13*b* schematically illustrates a second example of a cross-section of an actuator button.
Figure 13A:
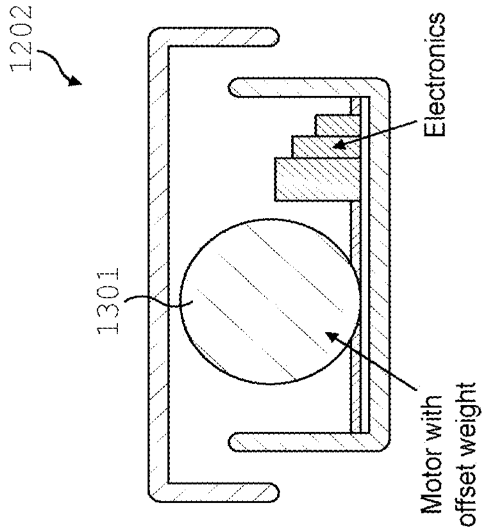
FIG. 13*a* schematically illustrates a first example of a cross-section of an actuator button.

In the case of the first insole 1001, the actuator/sensor buttons 1101, 1202 may be connected together and to a source of power by a top foil 1102 and/or a bottom foil 1103 (as shown in FIGS. 11 and 12). The top foil 1102 and the bottom foil 1103 are located on the top and bottom of the first insole 1001, respectively.

In the case of the second insole 1002, the actuator/sensor buttons 1202, 1101 may be connected together and to a source of power via electrically conductive wire (not shown) embedded in the connecting recesses 1004.

The button recesses 1003 are preferably circular for circumferentially equal displacement of weight from the user (when in use) into the surrounding insole body 1005. A circular shape of the button recesses 1003 also provides greater structural strength to the button recess and therefore helps protect the button provided therein from the weight of the user when the insole is in use.

The construction of the first insole 1001 is preferable for keeping manufacturing complexity low and is therefore more suitable for production in high volumes.

The construction of the second insole 1002 is preferable for protecting electrical connections between the buttons 1101, 1202 by providing connecting recesses 1004. This construction is therefore preferable for a more durable construction.

The insole body 1005 is preferably made from a rigid material such as a rigid polymer, for example acrylonitrile butadiene styrene (ABS) or polyether ether ketone (PEEK). An advantage of being manufactured from a rigid material is that the fragile components of the insole, such as the sensor buttons 1101, may be protected from the compressive force of the weight of the user when in use.

Figure 15:
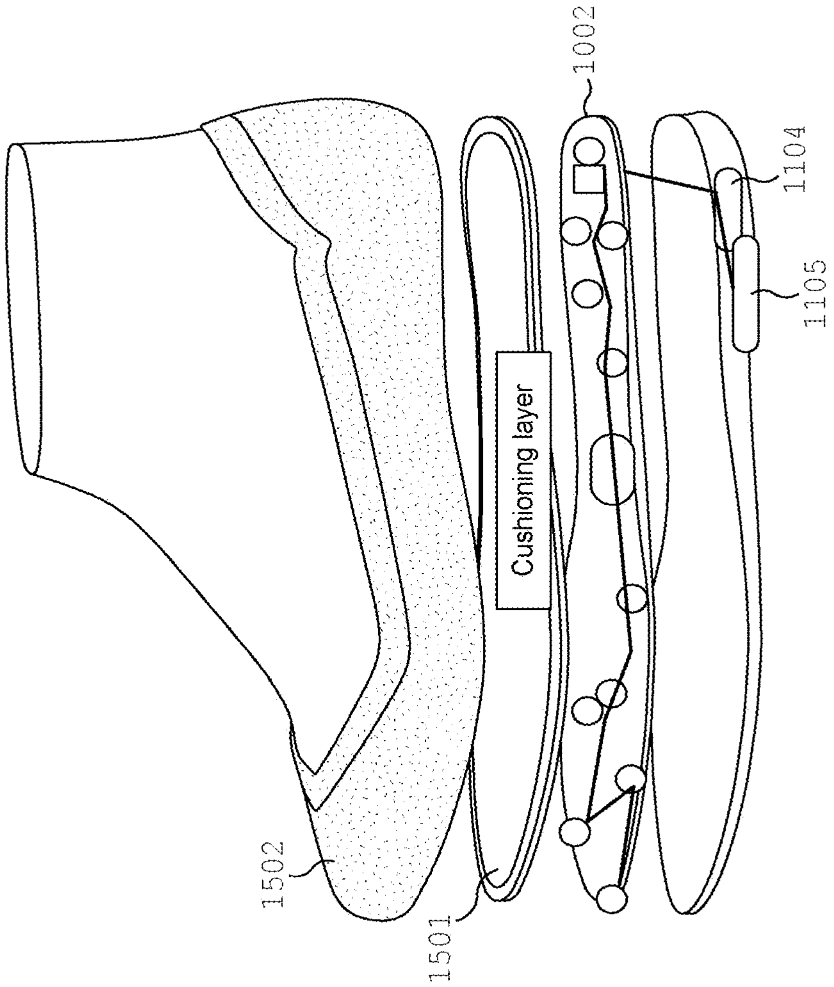
FIG. 15 illustrates a possible slipper or sock structure which may embody the invention.

As shown in FIG. 15, the article of footwear preferably comprises a cushioning layer 1501, more preferably located between the rigid insole 1002 and the fabric top 1502. An advantage of this arrangement is that it provides comfort to the user from the rigid insole 1002. A further advantage of this arrangement is to protect the electronic components of the rigid insole 1002 from the compressive force of the user's weight (in use).

The button recesses 1003 may be positioned on the insole body 1005 such that the positions correspond to the approximate locations of blood vessels on the sole of the user's foot. The button recesses 1003 may be positioned on the insole body 1005 such that the positions correspond approximately to reflexology points on the sole of the user's foot. The button recesses 1003 may be positioned on the insole body 1005 such that the positions correspond approximately to pressure points on the sole of the user's foot.

The insole may be manufactured using a method of additive manufacturing such as 3D printing. This is particularly advantageous for conforming the size and shape of the insole to the user's foot and for customising the locations of the button recess 1003 locations on the insole body 1005 for a given user.

A method of manufacturing the insole of the present disclosure may include the steps of scanning a user's foot and 3D printing an insole such that the size, shape and location of the button recesses 1003 conform to the user and their reflexology points and/or blood vessel locations.

Referring to FIGS. 11 and 12, the first insole 1001 or second insole 1002 may further comprise a top foil 1102 and a bottom foil 1103 for providing electrical connection between the buttons 1101, 1202. The top foil and the bottom foil are electrically conductive.

As shown in FIGS. 11 and 12, the sensor buttons 1101 and actuator buttons 1202 are sandwiched between the top foil 1102 and the bottom foil 1103. The two foils 1102, 1103 may be extended by wires to a controller 1104 and a battery 1105. The controller 1104 and battery 1105 may be located in a button recess 1003 of one of the insoles 1001, 1002, as illustrated in FIG. 11. Alternatively, the controller 1104 and battery 1105 may be located elsewhere on the person of the user, as illustrated in FIG. 12, preferably elsewhere in the footwear of the user (as illustrated in FIG. 15).

The top and bottom foils 1102, 1103 serve to distribute electrical power from the battery 1105 to the buttons 1102, 1201 and the controller 1104. The top and bottom foils 1102, 1103 may also provide bi-directional digital communication between the controller 1104 and the buttons. This may be achieved by a multiplexer multiplexing the data onto the power lines, which may be in the form of the top and bottom foils 1102, 1103.

The system may be controlled by a remote controller (not shown). The remote controller may be in communication with the controller 1104 by means of Bluetooth. The controller 1104 may therefore comprise a Bluetooth antenna 1106 which may be connected to a Bluetooth transmitter/receiver 1107. The remote controller may be a mobile telephone, smart watch or fitness device with Bluetooth functionality.

The battery 1105 may be rechargeable and may be recharged by means of a USB interface (not shown) in electrical connection with the controller 1104 and/or the battery 1105.

As shown in FIGS. 11 and 12, the sensor button 1101 may comprise an accelerometer 1108, a pressure sensor 1109, a sensor microprocessor 1110, a sensor flash memory 1111 and a sensor signalling interface 1112.

As shown in FIGS. 11 and 12, the controller 1104 may comprise the battery 1105, the Bluetooth transmitter/receiver 1107, the Bluetooth antenna 1106, a controller signalling interface 1113 and a controller microprocessor 1114.

As shown in FIG. 12, the actuator button 1202 may comprise an actuator 1203, an actuator signalling interface 1204, an actuator microprocessor 1205 and an actuator flash memory 1206.

As shown in FIGS. 13*a* and 13*b*, the actuator of the actuator button 1202 may be in the form of a motor with an offset weight 1301 (e.g. an eccentric motor). Alternatively, the actuator may be in the form of an electromagnet 1302 and coil 1303.

These above-mentioned components may be arranged to detect a pressure or several pressures on the sole of the foot and send the derived pressure data to the controller to be processed by the processor therein or presented to the user by means of a mobile application connected thereto. The pressure data once processed may initiate an actuation program for massaging the sole of the feet by sending instructions to the actuators.

Slipper Implementation

Figure 14:
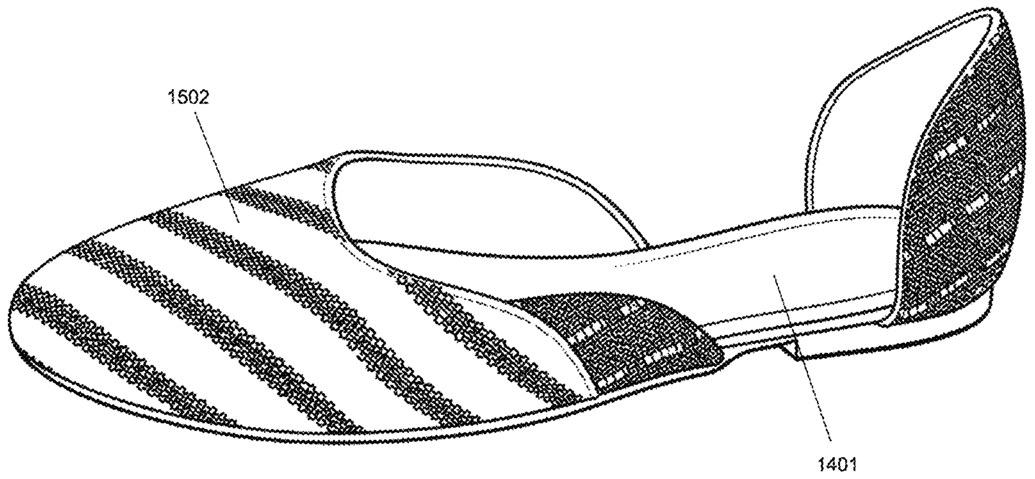
FIG. 14 illustrates a slipper which may embody the invention.

Referring to FIGS. 14 and 15, in one embodiment the article of footwear may be a slipper comprising a rigid sole 1401 and a fabric top 1502. More preferably, the fabric top 1502 comprises at least one elastic fibre for providing elastic tension around a circumference of the foot. More preferably, the fabric top 1502 comprises a pressure sensor for measuring blood pressure in the foot. More preferably, the pressure sensor comprises a stretch sensor located around the circumference of the foot.

An advantage of this embodiment of the invention is that a systolic and diastolic blood pressure reading can be taken.

The circumference of the foot may be around an arch of the foot. The circumference of the foot may alternatively be defined as around the ankle of the foot.

In the embodiments shown in FIGS. 14 and 15 the fabric top 1502 and rigid sole 1401 are in the form of a slipper. In an alternative embodiment (not shown), the fabric top may be in the form of a sock and the rigid sole may be a component of another item of footwear such as a shoe. In such an embodiment the sock may preferably comprise a means for electrically connecting the electrical components of the sock with the electrical components of the rigid sole. Such an electrical connection means may be in the form of an electrical circuit printed on to the fabric of the sock and a corresponding surface connection of the rigid sole such as the top foil 1102 shown in FIGS. 11 and 12. Alternatively, both the sock and the rigid sole may comprise wireless connection means for connecting to a common controller which may be preferably located in the rigid sole.

Figure 16:
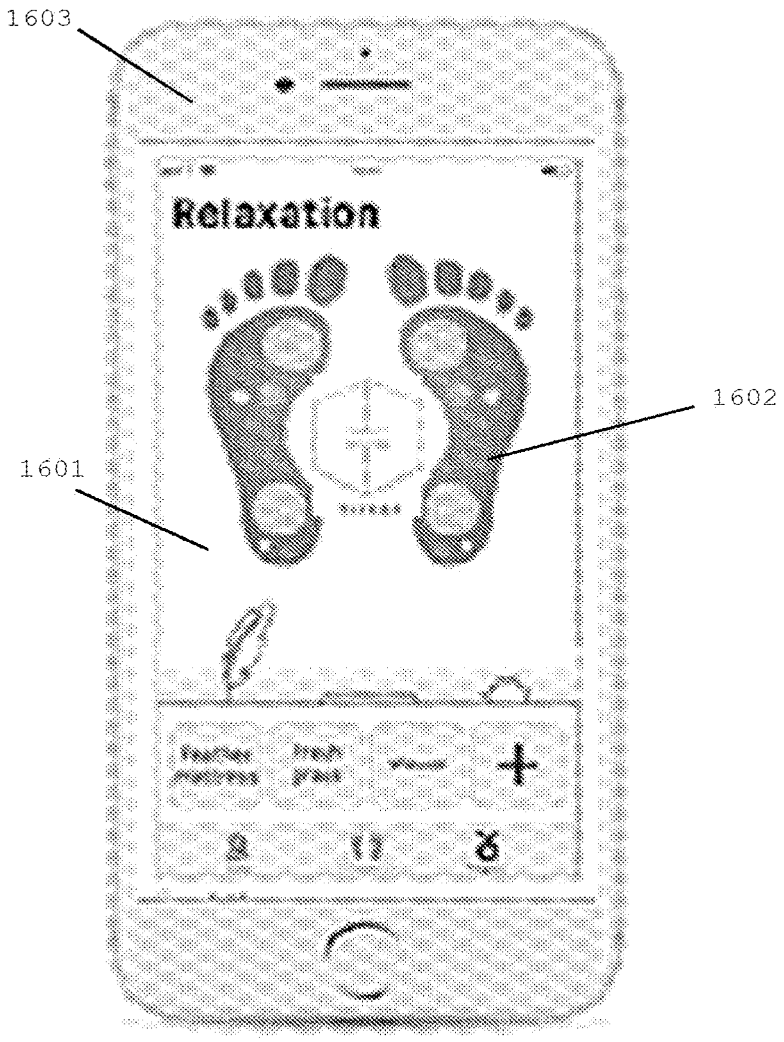
FIG. 16 illustrates a possible graphical user interface for a mobile application (e.g. on a smart phone) which may be used in an embodiment of the present invention.

FIG. 16 illustrates an example of a graphical user interface 1601 of a mobile application for use in controlling the system described above. The interface may comprise a representation of the user's feet 1602 on the touch screen of the mobile device which the user may touch to indicate where on the soles of their feet they would like actuation to take place. The mobile application may be executed on the user's mobile telephone 1603 (or other mobile telecommunication device such as a tablet computer) which, as discussed above, may be in Bluetooth communication with the controller 1104 of embodiments illustrated in FIGS. 11 and 12.

Figure 17:
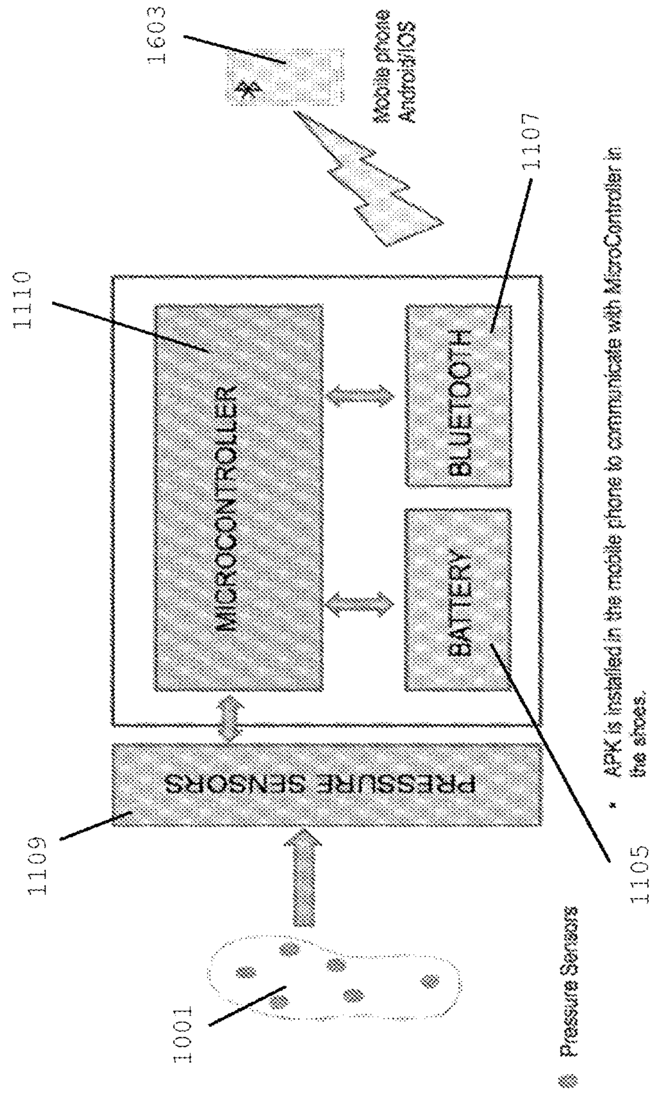
FIG. 17 schematically illustrates apparatus for providing power, connectivity and control to the pressure sensors.

FIG. 17 illustrates an overview of the control system shown in FIGS. 10, 11, 12 and 15.

The above embodiments may be arranged to carry out the operations illustrated in FIG. 9.

Such operations may include powering on of the system and awaiting configuration instructions. In the event that the system is being used for the first time, a new configuration may be applied via Bluetooth, otherwise the system uses an old configuration automatically.

The system may then identify the context to determine a power management procedure. If the article of footwear is not being worn then the system may go to sleep to conserve power. If a USB cable is connected the system may run a charging procedure. If the battery is low the system may sleep. If the article of footwear is being worn, the system may carry out a measuring strain and pressure procedure. If a massage is initiated over Bluetooth, a massage may be activated. During an active massage, if the battery is extremely low the system may go to sleep, if the massage is ended via Bluetooth or based on the amount of elapsed time the system may revert to a state of measuring strain and pressure.

The identifying context procedure may be initiated by the USB cable being unplugged, the article of footwear being taken off or the system powering on.

Further Aspects of the Present Work

The article of footwear may be an interactive smart shoe which detects high pressure points on the soles of the user's feet and delivers targeted massage to those key areas. Such a massage may stimulate some 7000 nerve endings. This may provide the advantage of helping ease foot fatigue, improve blood circulation and alleviate painful cold feet. This may be implemented through detection by the base sensors of key stress/pressure points and massage of the same by the actuators.

The base sensors may be acute pressure sensors and the actuators, through control by the microcontroller, may affect a pressure point massage.

The battery of the system may be rechargeable by wireless charging. This is advantageous in that no charge port is required on the surface of the article of footwear which would be vulnerable to the ingress of dirt and water.

In addition to the embedded sensors discussed above, the interactive smart shoe may further comprise haptic motors.

The key stress/pressure points may be shown on an accompanying mobile application, the likes of which are discussed above. The mobile application may perform a foot pressure analysis and activate a massage to stimulate the nerves of the feet.

By way of example, the article of footwear may comprise nine actuators, nine pressure sensors, an accelerometer, a Bluetooth transmitter/receiver, a wireless charger, a USB charging facility, an on/off switch located in the heel of the article and activated by clicking the heel, a lithium ion battery, a printed circuit board and firmware-software integration.

By way of example, the article may have the following specific features:

- Use 30 min per day
- Battery duration to last five days (minimising battery drainage)
- Battery life gauge/display on mobile application and LED indicator
- On/Off heel activation switch (manual)
- Massage intensity customised: different levels high/medium/low
- Mobile application integration and response time
- Software integration—feedback loop
- Withstand weight of 150 kg
- Water sealant/resistance to be worn as a regular shoe
- Electronic component unit length as per dimensions of largest and smallest insole (to be shared) and depth including casing of 3 mm
- Compatibility with iOS and Android
- Data storage
- Suitable for daily outdoor use: withstanding regular use/wear and tear—Shoe to be worn as a regular shoe
- Comfort is paramount and integration of electronics is seamless
- Massage intensity customised: different levels high/medium/low
- Pressure stress point mapping of foot

Possible Applications

- Footwear or socks, e.g. to measure foot pressure and provide massage/vibration therapy to the wearer's feet, thereby relieving stress and promoting health and well-being.
- Footwear or socks to massage a passenger's feet on an aeroplane, to help prevent deep vein thrombosis (such an article could be plugged-in to the aeroplane's electrical power supply, e.g. via a USB lead, or may alternatively be battery powered).
- Wearables (e.g. footwear or socks) to promote holistic wellbeing (targeting the reflex/vagus nerve to promote relaxation). The device may also incorporate one or more magnets for holistic wellbeing purposes.
- Wearables (e.g. footwear or socks) to promote context awareness.
- A learning sole that prevents fatigue.
- Footwear or socks for sportspeople, e.g.:
  - athletes (e.g. to monitor pressure across the foot when running or jumping);
  - football players (e.g. to monitor pressure across the foot when kicking a football, to determine which part of the foot is being used, and to help improve the player's technique);
  - racing drivers (e.g. monitoring accelerator foot pedal/shoe interaction; feedback from the pedals);
  - explorers;
  - soldiers (military boots);
  - water sport shoes (e.g. for surfing, diving—can incorporate safety/GPS/navigation features);
  - outdoor activity shoes (e.g. for hiking, mountain climbing—can provide rest/recuperation of soles).
- Wearables for sensory touch/haptic feedback (e.g. for virtual reality applications).
- Vehicle seat fabric (e.g. to measure pressure and provide massage/vibration therapy to the driver's or passenger's back, thereby relieving stress and promoting health, wellbeing and alertness).
- As part of a platform for developers/customisation, including haptic feedback to send a message through touch (e.g. a "hug shirt" or other wearable which provides sensory touch communication or interpersonal connectivity (e.g. a hug sensation) over a distance).
- Wearables (e.g. footwear or gloves) for the elderly to assist independent living—e.g. to provide early indicators of low grip strength or decreased muscle mass, to predict a risk of falling, to monitor vital signs (e.g. dehydration or low heart rate).
- Medical applications for higher resolution health care (e.g. personalisation, adaptation, monitoring & notifications, key to future discoveries, especially where patterns of disease are invisible to infrequent clinical observation).
- Integration with care planning.
- Remote monitoring.
- Longitudinal assessment.
- Decision support.
- Early warning & intervention.
- Applications to treat Parkinson's, multiple sclerosis, diabetic neuropathy (mobility aid to aid balance and reduce falls with those with sensory deficiencies), Alzheimer's, early detection of type 1 diabetics signs (loss of sensation in toes & ball of foot), rehabilitation, cerebral palsy, artificial limbs.

IoT in healthcare—e.g. remote monitoring to efficiently monitor health parameters. Doctors can easily track a patient's condition and determine critical insights, leading to a more advanced diagnosis process. This provides a solution to save both time and resources in hospitals, delivering real-time data to doctors. The device can send alerts to doctors' smart watches or smartphones, promoting more intensive care. Moreover the technology can be incorporated in artificial limbs and other supportive devices. Safety applications include real-time GPS tracking to detect locations efficiently, addressing women's and children's safety and aiding dementia patients.

Boots, socks or pads for animals' feet/hooves/paws—e.g. horse shoes, dressage recovery boots, sports boots, sensory wraps for horse training, jumping, riding and eventing. A particular issue is that, with horses, the vast majority of hoof cracks are secondary to poor hoof balance. This is often due to excessive or uneven load on a certain part of the hoof wall in stance or during motion. This causes damage to the tubular horn structure within the hoof wall, causing it to weaken and split. Monitoring of the pressure exerted on a horse's hooves, using a horse boot embodiment of the present invention, can lead to fatigue/injury prevention. No horse has 100% balanced feet and we can only endeavour to gradually make changes to try and achieve balance as close as possible for the individual horse. Foot placement will give an insight into the sites of impact and the possible leveraging forces exerted on the hoof wall. Embodiments can also provide treatment of the aches, pains and strains that can occur to a horse's hooves during training and in competition, to provide prophylactic physiotherapy.

Personalised wellbeing: the present work may also be used in the promotion of wellbeing through personalised measurement and actuation. Example applications may include: postural alignment; adjustment in accordance with a user's weight; the use in the application of healthcare through data gathered from use of the present work in conjunction with artificial intelligence; wellness measurement; use as a diagnostic tool; and localised pain management.

Other applications are also possible, as those skilled in the art will appreciate.

Possible Modifications and Alternatives

Detailed embodiments and some possible alternatives have been described above. As those skilled in the art will appreciate, a number of modifications and further alternatives can be made to the above embodiments whilst still benefiting from the inventions embodied therein. It will therefore be understood that the invention is not limited to the described embodiments and encompasses modifications apparent to those skilled in the art lying within the scope of the appended claims.

For instance, in respect of the implementation described above with reference to FIG. 3, in one variant the power supply module 102 may be referred to as a "current-feeding module" (CFM), and the analysis module 103 may be referred to as a "current-sensing module" or "current-sourcing module" (CSM). The CFM 102 is configured to create a current, the characteristics of which are known, and to analyse changes caused by the CSM 103. The CSM 103 is configured to source the current fed by the CFM 102 and to modify and analyse the results.

Further, in respect of the implementation described above with reference to FIG. 4, in one variant (as may be applied to an insole, for instance) the power supply module 102 may be referred to as a "current-feeding module" (CFM), and the analysis module 103 may be referred to as a "current-sensing module" or "current-sourcing module" (CSM). The CFM 102 is configured to send an identifying signal to the e.g. insole, in addition to reading characteristics. The CSM 103 is configured to source the identifying signal, and to act according to CFM controls. The CSM 103 can provide electrical comparison for the CFM 102.

Summary

Amongst other things, the present work provides a knitted or woven structure, said structure comprising conductive and nonconductive parts, a computational structure, a power supplying structure, a sensing structure and an actuating structure, which may be knitted or woven as an open form intended for wrapping around a limb, or as a tubular form open at both ends intended for sheathing a limb, or as a tubular form open from one end intended for sheathing a limb, with conductive and non-conductive area or areas made with different types of yarns, filaments or other suitable textile materials, which may comprise electroactive materials or electrical or electronic components, including but not limited to microprocessors, sensors, actuators, power supplies, and batteries.

The system described in the present work is primarily intended for healthcare, with a knitted or woven structure supporting this use through a possibility for real-time analysis, and connectivity to smart phones or other systems, such as Artificial Intelligence through wireless data transfer. The system described is capable of independent as well as connected behaviour.

The present work solves a problem of arranging or manufacturing computational structures to a knitted or woven structure within a casing suitable for attaching to a limb, such as but not limited to a shoe or a structure to be worn for ambulatory movement, in such a way that it does not inhibit the movement of the wearer, while providing electronic functionality within the knitted or woven structure.

The present work also provides a system for improving blood circulation, the system comprising a control unit comprising a processor and at least one article of footwear wherein one or more of the at least one articles of footwear together or alone comprise: one or more actuators coupled to and controlled by the control unit; and a flexible wearable material comprising: one or more electrically-conductive paths; and one or more sensors integrated into the wearable material and coupled to the processor, for providing measurement signals to the control unit; the system further comprising an electrical power supply for supplying electrical power to the one or more sensors by means of the one or more electrically-conductive paths.

The present work also provides a system for improving blood circulation, the system comprising a control unit comprising a processor and at least one article of footwear wherein one or more of the at least one articles of footwear together or alone comprise: one or more actuators coupled to and controlled by the control unit; one or more electrically-conductive paths; one or more sensors integrated into the at least one article of footwear and coupled to the processor, for providing measurement signals to the control unit; and the system further comprising an electrical power supply for supplying electrical power to the one or more sensors by means of the one or more electrically-conductive paths.

The invention claimed is:

1. A system for improving blood circulation, the system comprising a control unit comprising a processor and at least one article of footwear, wherein one or more of the at least one articles of footwear together or alone comprise:

one or more actuators coupled to and controlled by the control unit;

wherein the control unit further comprises of a control module, a power supply module, and an analysis module, the control unit configured such that the entire control unit is embedded into the at least one article of footwear;

one or more electrically-conductive paths; and one or more sensors integrated into the at least one article of footwear and coupled to the processor, for providing measurement signals to the control unit;

the power module for supplying electrical power to the one or more sensors by means of the one or more electrically-conductive paths;

wherein the analysis module is configured to identify the high stress points from the measurement signals received from the one or more sensors, and wherein the one or more actuators comprise one or more motors configured to provide a vibration/massage function comprising a tailored massage localised to an area of the sole of a user comprising high stress points identified by the analysis module; and the at least one article of footwear is configured to incorporate a platform embedded in the at least one article of footwear to facilitate connecting the user to at least one other device, wherein the platform is further configured to enable communication with a medical practitioner and/or health service.

2. The system according to claim 1, wherein the rigid base comprises one or more recesses for receiving one or more of said actuators and/or one or more sensors.

3. The system according to claim 1, further comprising a flexible wearable material which comprises at least one elastic fibre for providing pressure around the circumference of the foot.

4. The system according to claim 3, wherein the one or more sensors integrated into the wearable material comprise a pressure sensor for measuring blood pressure.

5. The system according to claim 1, wherein the control unit is configured to activate the one or more actuators in response to a measurement signal received from the one or more sensors satisfying a predetermined condition.

6. The system according to claim 3, wherein the flexible wearable material comprises a knitted or woven fabric.

7. The system according to claim 6, wherein the one or more electrically-conductive paths are formed of electrically-conductive yarn within the fabric.

8. The system according to claim 7, wherein the one or more sensors are attached to the electrically-conductive yarn.

9. The system according to claim 1, wherein the article of footwear comprises a 3D-printed material.

10. The system according to claim 1, wherein the electrical power supply comprises a battery.

11. The system according to claim 1, wherein the electrical power supply comprises an input via which electrical power may be received from elsewhere.

12. The system according to claim 1, wherein the one or more sensors are selected from a group comprising: pressure sensors, temperature sensors, biosensors, moisture sensors, accelerometers and inclinometers.

13. The system according to claim 1, wherein the one or more actuators comprise one or more heating elements.

14. The system according to claim 1, wherein said at least one article of footwear is a massage shoe.

15. The system according to claim 1, further comprising an insole, wherein the insole comprises at least one electrically conductive foil.

16. The system according to claim 15, wherein the at least electrically conductive foil is arranged to receive and/or distribute electrical power multiplexed with at least one data signal.

17. The system according to claim 1, further comprising an insole, wherein the insole comprises at least one recess for receiving at least one button.

18. The system according to claim 1, further comprising an insole, wherein the insole further comprises at least one sensor button and/or at least one actuator button.

19. The system according to claim 1, wherein the system further comprises a mobile application configured to display the high stress points.

20. The system according to claim 1, wherein the article of footwear further comprises a rigid base.

* * * * *